(12) United States Patent
Rencurosi et al.

(10) Patent No.: US 10,011,605 B2
(45) Date of Patent: Jul. 3, 2018

(54) PROCESS FOR THE PREPARATION OF TRIAZOLO[4,5-D] PYRIMIDINE CYCLOPENTANE COMPOUNDS

(71) Applicant: FLAMMA SPA, Chignolo d'Isola (IT)

(72) Inventors: Anna Rencurosi, Melzo (IT); Massimo Previtali, Castelleone (IT); Federico Della Negra, Padua (IT); Francesco Mormile, Albino (IT); Renato Canevotti, Concorezzo (IT)

(73) Assignee: FLAMMA SPA, Chignolo d'Isola (IT)

(*) Notice: Subject to any disclaimer, the term of this patent is extended or adjusted under 35 U.S.C. 154(b) by 0 days.

(21) Appl. No.: 15/319,193

(22) PCT Filed: Jun. 11, 2015

(86) PCT No.: PCT/EP2015/063040
§ 371 (c)(1),
(2) Date: Dec. 15, 2016

(87) PCT Pub. No.: WO2015/193165
PCT Pub. Date: Dec. 23, 2015

(65) Prior Publication Data
US 2017/0129898 A1    May 11, 2017

(30) Foreign Application Priority Data

Jun. 18, 2014 (IT) .............................. MI2014A1096

(51) Int. Cl.
*C07D 487/04* (2006.01)
*C07D 239/48* (2006.01)
*C07D 239/46* (2006.01)
*C07D 239/50* (2006.01)

(52) U.S. Cl.
CPC ......... *C07D 487/04* (2013.01); *C07D 239/46* (2013.01); *C07D 239/48* (2013.01); *C07D 239/50* (2013.01)

(58) Field of Classification Search
CPC .. C07D 239/46; C07D 239/50; C07D 487/04; C07D 317/06
USPC ................................................. 544/254, 318
See application file for complete search history.

(56) References Cited

U.S. PATENT DOCUMENTS

| 6,251,910 B1 | 6/2001 | Guile et al. |
| 6,525,060 B1 | 2/2003 | Hardern et al. |
| 6,974,868 B2 | 12/2005 | Hardern et al. |
| 7,067,663 B2 | 6/2006 | Larsson et al. |
| 7,122,695 B2 | 10/2006 | Clark et al. |
| 7,250,419 B2 | 7/2007 | Hardern et al. |
| 2007/0265282 A1 | 11/2007 | Hardern et al. |
| 2008/0132719 A1 | 6/2008 | Dejonghe et al. |
| 2008/0214812 A1 | 9/2008 | Hardern et al. |
| 2015/0005498 A1* | 1/2015 | Maras ................. C07D 405/12 544/254 |

FOREIGN PATENT DOCUMENTS

| CN | 102311437 | 1/2012 |
| CN | 102675321 | 9/2012 |
| CN | 102875537 | 1/2013 |
| CN | 103130726 | 6/2013 |
| EP | 0 996 621 | 10/2003 |
| EP | 1 135 391 | 3/2004 |
| WO | 2008/018823 | 2/2008 |
| WO | 2010/030224 | 3/2010 |
| WO | 2012/085665 | 6/2012 |
| WO | 2012/138981 | 10/2012 |
| WO | 2013/023511 | 2/2013 |
| WO | 2013/037942 | 3/2013 |
| WO | 2013/060837 | 5/2013 |

OTHER PUBLICATIONS

International Search Report dated Jul. 15, 2015 in International (PCT) Application No. PCT/EP2015/063040.
Written Opinion of the International Searching Authority dated Jul. 15, 2015 in International (PCT) Application No. PCT/EP2015/063040.
Costa et al., "Simple reduction of ethyl, isopropyl and benzyl aromatic esters to alcohols using sodium borohydride-methanol system", ARKIVOC, 2006, pp. 128-133, ISSN 1424-6376.
Springthorpe et al., "From ATP to AZD6140: The discovery of an orally active reversible $P2Y_{12}$ receptor antagonist for the prevention of thrombosis", Bioorganic & Medicinal Chemistry Letters, vol. 17, 2007, pp. 6013-6018.
Babulreddy et al., "Synthesis, Characterization and Antimicrobial Screening of New Class of 1-Substituted-N-(1,2,3,4-Tetrahydronaphthalen-1-YL)-1H-Benzo[D] [1,2,3]Triazole-5-Caboxamide Derivatives", http ://heteroletters.org (online), vol. 2, No. 3, 2012, pp. 253-261, ISSN: 2231-3087.

* cited by examiner

Primary Examiner — Venkataraman Balasubramanian
(74) Attorney, Agent, or Firm — Wenderoth, Lind & Ponack, L.L.P.

(57) ABSTRACT

The present invention relates to a process for preparation of triazolo[4,5-d] pyrimidine cyclopentane compounds of formula (I), and pharmaceutically acceptable salts thereof. The invention also provides novel compounds that can be used as intermediates in the process for preparing triazolo[4,5-d] pyrimidine cyclopentane compounds. The process and the intermediates are particularly useful for the preparation of ticagrelor and pharmaceutically acceptable salts thereof.

32 Claims, 1 Drawing Sheet

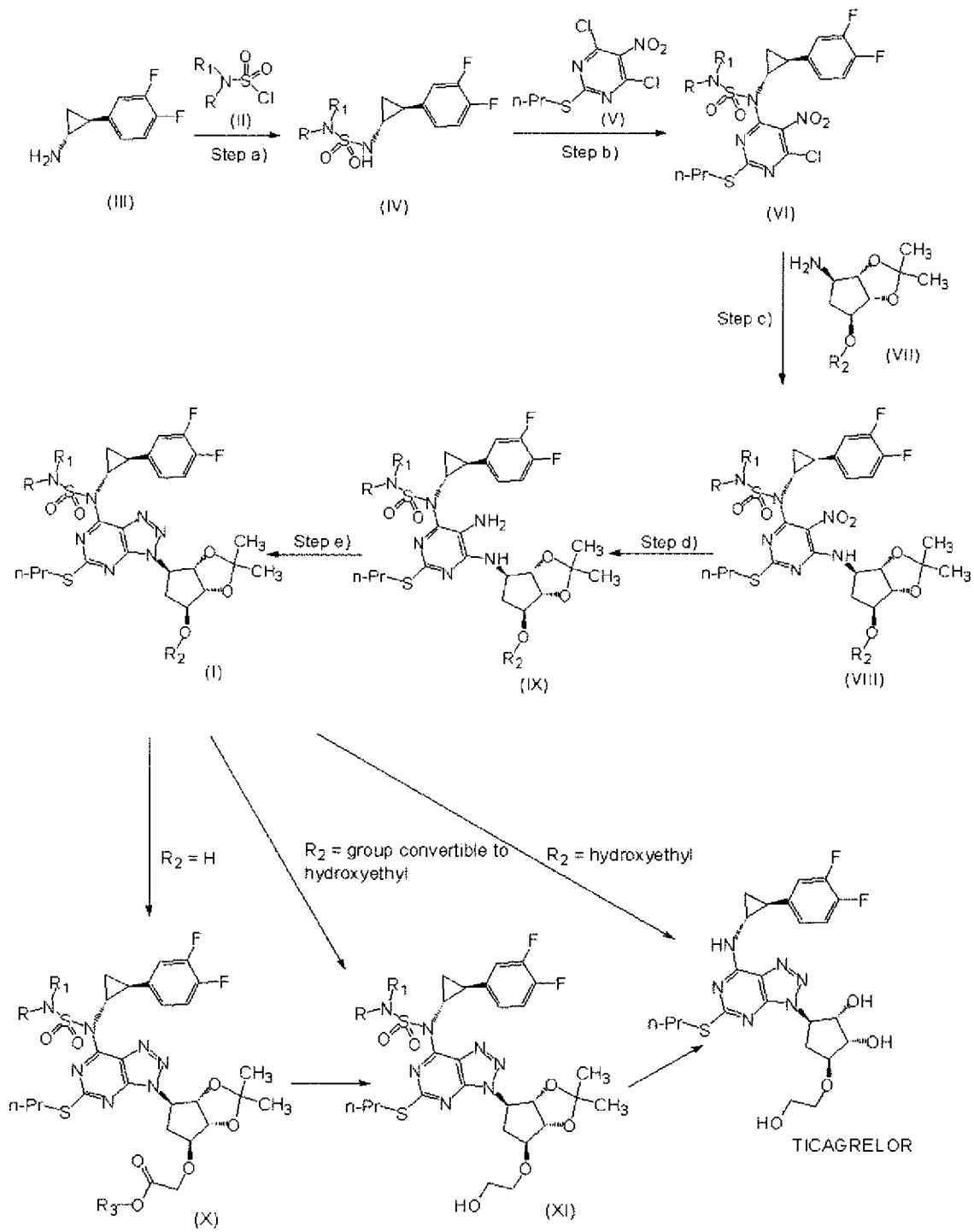

PROCESS FOR THE PREPARATION OF TRIAZOLO[4,5-D] PYRIMIDINE CYCLOPENTANE COMPOUNDS

The present invention relates to a process for the preparation of triazolo[4,5-d] pyrimidine cyclopentane compounds and pharmaceutically acceptable salts thereof.

The invention also provides novel compounds that can be used as intermediates in the process for preparing triazolo [4,5-d] pyrimidine cyclopentane compounds.

STATE OF THE ART

Various processes for the preparation of triazolo[4,5-d] pyrimidine cyclopentane compounds, related derivatives and pharmaceutically acceptable salts thereof are disclosed in U.S. Pat. No. 6,251,910; U.S. Pat. No. 6,525,060; U.S. Pat. No. 6,974,868; U.S. Pat. No. 7,067,663; U.S. Pat. No. 7,122,695, U.S. Pat. No. 7,250,419; US2007/0265282, US2008/0132719, US2008/0214812. EP0996621, EP1135391; CN102311437, CN102875537, CN102675321, CN103130726, WO2008/018823, WO2010/030224, WO2012138981, WO2013060837 and WO 2013023511.

Ticagrelor is an important triazolo[4,5-d] pyrimidine cyclopentane compound that acts as as an adenosine uptake inhibitor, a platelet aggregation inhibitor, a P2Y12 purinoceptor antagonist and a coagulation inhibitor. Ticagrelor, (1S,2S,3R,5S)-3-[7-[(1R,2S)-2-(3,4-difluorophenyl)cyclopropylamino]-5-(propylthio)-3H-[1,2,3] triazolo[4,5-d]pyrimidin-3-yl]-5-(2-hydroxyethoxy)cyclopentane-1,2-diol, is represented by the following structural formula

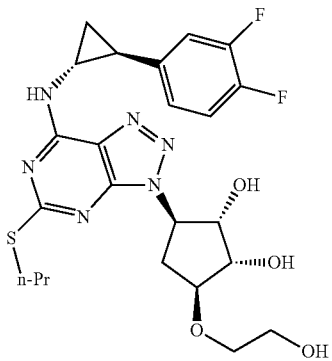

Ticagrelor and derivatives thereof can be obtained by the process described in WO2012/085665, which comprises the steps of preparing an intermediate of the following formula:

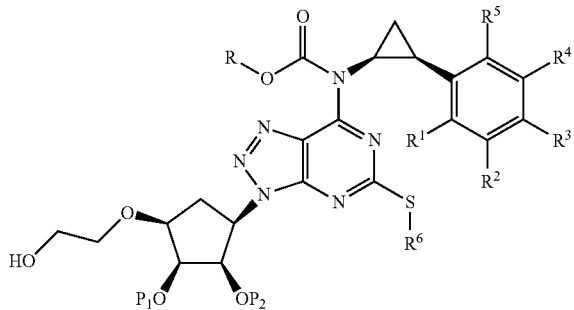

wherein R is a $C_{1-6}$ alkyl or an optionally substituted benzyl.

WO2013/037942 discloses processes for preparing ticagrelor via either the intermediate of formula

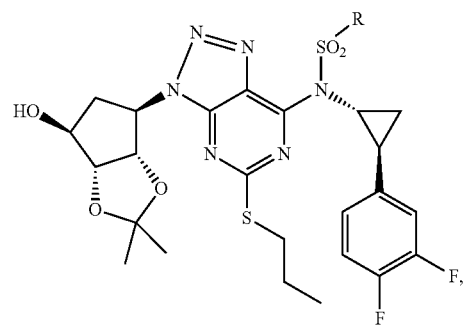

wherein R is specifically indicated as p-tolyl, benzenesulfonyl or 2-naphtyl. or via the intermediate of formula

BRIEF DESCRIPTION OF THE DRAWINGS

An embodiment of the overall process for preparing ticagrelor is summarized in FIG. 1.

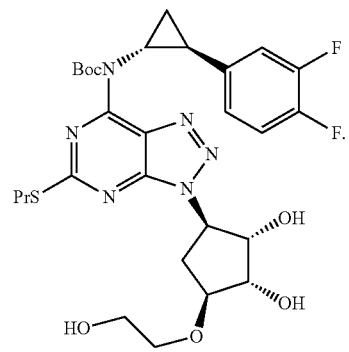

The processes for the preparation of triazolo[4,5-d] pyrimidine cyclopentane compounds, ticagrelor and related compounds described in the above mentioned prior art suffer from many disadvantages, since they involve tedious and cumbersome procedures such as lengthy and multiple synthesis steps, column chromatographic purifications, use of hazardous materials like isoamyl nitrite, bromoform, diazomethane and sodium azide and resulting in low overall yields of the product.

Therefore, there exists a need to develop an improved process for obtaining triazolo[4,5-d] pyrimidine cyclopentane compounds, including ticagrelor, which is cost effective, easily scalable and suitable for industrial use.

DESCRIPTION OF THE INVENTION

The present invention provides an industrially applicable and economically improved process for the preparation of triazolo[4,5-d] pyrimidine cyclopentane compounds and pharmaceutically acceptable salts thereof, which are themselves useful materials for the synthesis of ticagrelor and pharmaceutically acceptable salts thereof.

The invention also provides novel compounds that can be used as intermediates in the process for preparing said triazolo[4,5-d] pyrimidine cyclopentane compounds.

A further object of the present invention provides a process for the preparation of ticagrelor.

All of the terms that are used therein should be understood in their conventional meaning as they are known in the art unless indicated to the contrary. Other more specific definitions for some terms as used therein are given below and always apply throughout the description and the claims unless a different definition explicitly gives a wider definition.

The term "$C_1$-$C_6$ alkyl" refers to a branched or linear hydrocarbon containing from 1 to 6 carbon atoms. Examples of $C_1$-$C_6$ alkyl groups include but are not limited to methyl, ethyl, n-propyl, isopropyl, n-butyl, sec-butyl, isobutyl, tert-butyl, n-pentyl, n-hexyl. The $C_1$-$C_6$ alkyl may optionally be substituted with one or more electron-attractor groups.

The term "one pot" refers to two or more consecutive reactions which are carried out without isolating the respective intermediate product or products.

The term "pharmaceutically acceptable salt" refers to a non-toxic inorganic or organic salt. Examples of pharmaceutically acceptable salts include but are not limited to: carbonate, hydrochloride, hydrobromide, sulphate, hydrogen sulphate, citrate, maleate, fumarate, trifluoroacetate, 2-naphthalenesulphonate, and para-toluenesulphonate. Further information on pharmaceutically acceptable salts can be found in pharmaceutical chemistry manuals, for example: *Handbook of pharmaceutical salts*, P. Stahl, C. Wermuth, WILEY-VCH (Eds., 2008, pp. 127-133), herein incorporated by reference.

As used herein, the term "strong base" refers to a base that is able to deprotonate a hydroxyl group, such as a hydroxyl group directly bonded to an alkane moiety. Examples of such strong bases include, but are not limited to, alkyllithiums, metal amides, metal hydrides, metal dialkylamides and arylamines, wherein: alkyllithiums include isobutyllithium, n-hexyllithium, n-octyllithium, butyllithium, s-butyllithium, t-butyllithium, phenyllithium and triphenylmethyllithium; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The term "reducing agent for nitro groups" refers to any agent which is capable of converting a nitro group into the corresponding amine. Many methods for the reduction of nitro groups into amine exist, such as: catalytic hydrogenation using palladium-on-carbon, platinum(IV) oxide, or Raney nickel, iron in acidic media, sodium hydrosulfite, sodium sulfide, sodium dithionite, formamidine sulfinic acid, tin(II) chloride, zinc.

The term "reducing agent for ester groups" is understood to mean, according to the present invention, any agent which is capable of converting a carboxilyc group into the corresponding alcohol. A variety of reducing agents are well known in the art (for example, see, e.g., R. Larock, "Comprehensive Organic Transformations", VCH Publishers, Inc., 1989). Examples of suitable reducing agent for ester groups include hydride reducing agents, boranes and hydrogenation over copper chromite catalyst or Ru catalyst over charcoal. Preferred hydride reducing agents are sodium borohydride, lithium borohydride, DIBAL-H, lithium aluminum hydride; preferred boranes include diborane and $BH_3$—$SMe_2$ in refluxing tetrahydrofuran. The term "group convertible to hydroxyethyl" according to the present invention refers to a group consisting of: —$CH_2COOR_3$, wherein $R_3$ is a $C_1$-$C_6$-alkyl; cyanomethyl; —$CH_2CH(E_1R^i)(E_2R^{ii})$, wherein $E_1$ and $E_2$ are independently selected from a chalcogen element, preferably O or S, and $R^i$ and $R^{ii}$ are the same or different, selected from $C_1$-$C_4$-alkyl, or together form $C_2$-$C_4$-alkylene or o-phenylene connection; or —$CH_2CH_2$—$OR^{iii}$ wherein $R^{iii}$ is a hydroxy protecting group, selected from tertiary alkyl group, preferably tert-butyl or trityl, arylmethyl group, preferably benzyl or para substituted benzyl, methoxy substituted $C_1$-$C_2$-alkyl group, preferably methoxymethyl (MOM), trisubstituted silyl group, preferably trimetylsilyl, tert-butyldimethylsilyl (TBDMS) or tert-butyldiphenylsilyl, acyl, preferably pivaloyl or benzoyl. Preferred group convertible to hydroxyethyl groups are selected from —$CH_2COOMe$, —$CH_2COOEt$, tert-butoxyethyl, trityloxyethyl. and benzyloxyethyl.

The object of the present invention is a process for the preparation of triazolo[4,5-d]pyrimidine cyclopentane compounds of formula I:

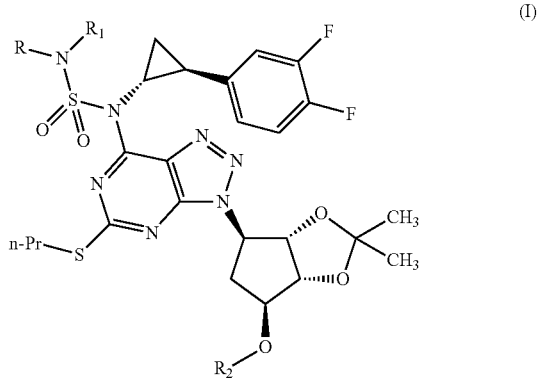

(I)

and pharmaceutically acceptable salts thereof, wherein R and $R_1$ are, independently of each other, $C_1$-$C_6$-alkyl or benzyl; or R and $R_1$ are taken together with the nitrogen atom to which they are attached to form a 5 to 6 membered heterocyclic ring, optionally substituted by one or more $C_1$-$C_6$ alkyl group, $R_2$ is hydrogen, hydroxyethyl or a group convertible to hydroxyethyl, which process is characterized by comprising at least one of the following steps:

a) reacting a compound of formula II

(II)

wherein R and $R_1$ are as above defined, with a compound of formula III

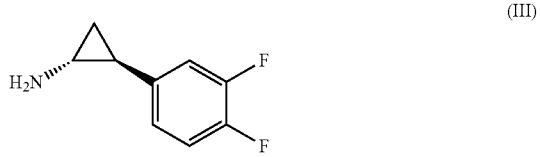 [SMILES: N[C@@H]1C[C@H]1c1ccc(F)c(F)c1]

(III)

to obtain a compound of formula IV

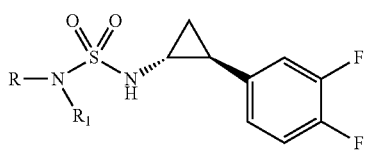
(IV)

wherein R and R₁ are as above defined;
b) reacting a compound of formula IV with a compound of formula V

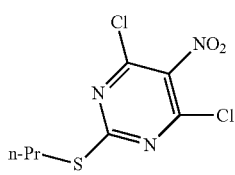
(V)

to obtain a compound of formula VI

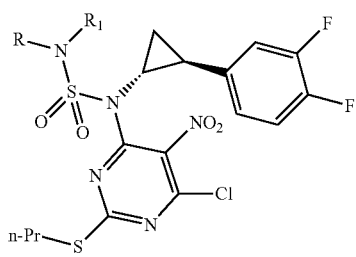
(VI)

wherein R and R₁ are as above defined;
c) reacting a compound of formula VI with a compound of formula VII or a salt thereof

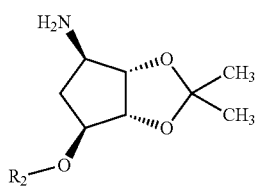
(VII)

wherein R₂ is as above defined, to give a compound of formula VIII:

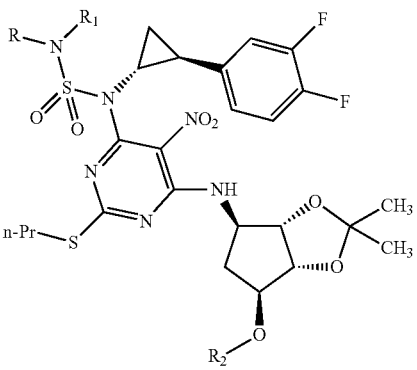
(VIII)

wherein R, R₁ and R₂ are as above defined;
d) reducing the nitro group of a compound of formula VIII to obtain a compound of formula IX:

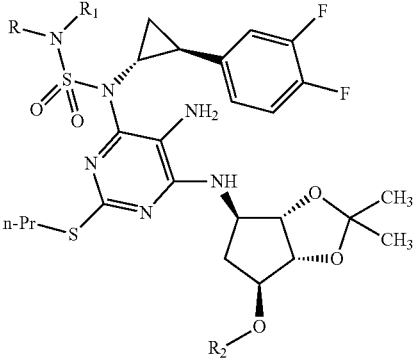
(IX)

wherein R, R₁ and R₂ are as above defined;
e) nitrosating a compound of formula IX.

Step a) may be performed in an organic solvent in the presence of a tertiary amine.

The organic solvent may be preferably an aprotic organic solvent, more preferably it is selected among the group comprising toluene, benzene, tetrahydrofurane, dichloromethane. In one preferred embodiment the aprotic solvent is toluene. Suitable tertiary amines are triethylamine (TEA), diisopropylethylamine (DIPEA), 1,8-diazabicyclo[5.4.0]undec-7-ene (DBU) and 1,4-diazabicyclo[2.2.2]octane (DABCO) and mixtures thereof.

Preferably, each of R and R₁ in the compound of formula II is a methyl group.

The molar ratio of the compound of formula II to the compound of formula III is preferably between 10 and 0.5 more preferably between 1.5 and 1.

The molar ratio of the compound of formula II to the tertiary amine is preferably between 1 and 0.1, more preferably between 0.7 and 0.8.

The reaction is performed at a temperature between 0° C. and the reflux temperature of the solvent, more preferably between 10 and 20° C.

The ratio of the organic solvent to the compound of formula II is preferably between 50 and 2 by weight, more preferably between 10 and 5 by weight The compound of formula IV thus obtained can be isolated by separation techniques well known to persons skilled in the art, such as: extraction, filtration, crystallization, precipitation, and the like.

The compound of formula IV is preferably isolated as a solid by filtration after slurring the crude product in a suitable organic solvent at a temperature comprised between 10 and 50° C.

Preferred solvents are aprotic apolar solvents such as aliphatic or aromatic hydrocarbons including pentane, hexane, cyclohexane, heptane, toluene, benzene. In one embodiment, the compound of formula IV is isolated as a solid by filtration after slurring the crude product in heptane at a temperature between 20 and 40° C. Step b) may be performed in an organic solvent in the presence of a base. The organic solvent is preferably an aprotic dipolar solvent. Possible aprotic dipolar solvents are tetrahydrofuran methyl-tetrahydrofuran, isopropyl acetate, methyl-isobutyl-ketone, dimethylformamide, acetonitrile, N-methyl-pyrrolidone, dimethyl sulfoxide Preferably, the aprotic dipolar solvent is acetonitrile.

The ratio of the organic solvent to the compound of formula V is preferably between 50 and 5 by weight, more preferably between 15 and 10 by weight.

The base is preferably an inorganic base, more preferably is potassium phosphate or potassium carbonate.

The molar ratio of the compound of formula IV to the compound of formula V is preferably between 1.1 and 0.9.

The reaction is performed at a temperature between 10 and reflux temperature of the selected solvent, more preferably between 20 and 30° C.

The reaction mass containing the compound of formula VI may be subjected to usual work up or may be used directly in the next step to produce the compound of formula VIII without isolation. Preferably, the reaction mass containing the compound of formula VI is used directly in the next step without isolation.

Steps b) and c) may thus be carried out in one-pot to achieve the compound of formula VIII.

Step c) may be performed in an organic solvent in the presence of a base. The base is preferably an inorganic base, more preferably is potassium phosphate or potassium carbonate.

The organic solvent is preferably an aprotic dipolar solvent. Possible aprotic dipolar solvents are tetrahydrofuran, methyl-tetrahydrofuran, isopropyl acetate, methyl-isobutyl-ketone, N,N-dimethylformamide, acetonitrile, dimethyl sulfoxide. Preferably, the aprotic dipolar solvent is acetonitrile.

The ratio of the organic solvent to the compound of formula VI is preferably between 50 and 5 by weight, more preferably between 15 and 10 by weight.

The molar ratio of the compound of formula VII to the compound of formula VI is preferably between 0.5 and 5, more preferably between 1.0 and 1.5.

In one embodiment, a compound of formula VI is reacted with a salt of a compound of formula VII.

Suitable salts of the compound of formula VII are: chloric acid salt, oxalic acid salt, succinic acid salt, mandelic acid salt, m-Cl-mandelic acid salt, L-tartaric acid salt, dibenzoyl-L-tartaric acid salt, protected amino acid salts such as Boc-L-lucine salt, Boc-L-phenylalanine salt.

Preferably, the salt of the compound of formula VII wherein $R_2$ is hydroxyethyl, is a L-tartaric acid salt.

In accordance with one embodiment of the present invention wherein step b) and step c) are carried out in one-pot to achieve the compound of formula VIII, the molar ratio of the compound of formula VII to the compound of formula IV is preferably between 0.5 and 5, more preferably between 1.0 and 1.5.

The reaction is performed at a temperature between 10° C. and the reflux temperature of the selected solvent, more preferably between 25 and 45° C.

The compound of formula VIII can be isolated by separation techniques well known to persons skilled in the art, such as: extraction, filtration, crystallization, precipitation, and the like.

The compound of formula VIII is preferably isolated as a solid by filtration after dissolution of the crude product in a suitable organic solvent at a temperature comprised between 25° C. and the reflux temperature of the solvent, followed by contacting the thus obtained solution with water.

Water may be added to the thus obtained solution or, alternatively, the thus obtained solution may be added to water.

In an embodiment the organic solvent is a protic or aprotic dipolar solvent such as methanol, ethanol, iso-propanol, butanol, tetrahydrofuran, acetone, N,N-dimethylformamide, acetonitrile, dimethyl sulfoxide. Preferably, the solvent is N,N-dimethyl formamide.

The ratio of the organic solvent to the compound of formula VIII is preferably between 20 and 1 by weight, more preferably between 5 and 1 by weight.

In one embodiment, the compound of formula VIII wherein $R_2$ is hydroxyethyl is dissolved in N,N-dimethyl-formamide and isolated as a solid after addition of the thus obtained solution to water.

Step d) may be performed in an organic solvent in the presence of a suitable reducing agent for nitro groups.

Alternatively, the reduction may be carried out by catalytic hydrogenation.

The catalytic hydrogenation is performed at a temperature between 10 and 50° C., more preferably between 15 and 25° C.

The organic solvent is preferably a polar protic solvent. Possible polar protic solvents are water, alcohols, formic acid and mixtures thereof. Preferably, the polar protic solvent is methanol or a mixture of water and methanol.

The ratio of the organic solvent to the compound of formula VIII is preferably between 50 and 4 by weight, more preferably between 10 and 4 by weight.

The catalytic hydrogenation is preferably carried out using palladium-on-carbon, palladium-on-carbon in the presence of ammonium formate, platinum(IV)oxide, or Raney nickel.

In one embodiment the catalytic hydrogenation is carried out in a polar protic solvent in the presence of palladium-on-carbon catalyst at a temperature between 20 and 40° C., at a pressure between 1-5 bar, thus obtaining a compound of formula IX.

The nitrosating reaction of step e) may be performed with any nitrosating agent in an acidic medium.

Possible nitrosating agents are isoamyl-nitrite, butyl-nitrite, sodium nitrite, potassium nitrite and lithium nitrite.

The nitrosating reaction wherein the nitrosating agent is isoamyl-nitrite may be performed according to "Bioorganic & Medicinal Chemistry Letters 17 (2007) 6013-6018", herein incorporated by reference.

Possible acidic medium used in the nitrosating reaction include organic acids.

In one embodiment, the acidic medium is preferably acetic acid.

The use of the nitrosating agent sodium nitrite in acetic acid is disclosed for example in "Babulreddy, A. et at., Heterocyclic Letters, 2(3), 253-261; 2012", herein incorporated by reference.

The molar ratio of the compound of formula IX to the nitrosating agent is preferably between 1 and 0.2, more preferably between 0.9 and 0.7.

The reaction is performed at a temperature between 15 and 50° C., more preferably between 20 and 30° C.

The reaction may be performed in the further presence of an organic solvent. In an embodiment the organic solvent is a protic or an aprotic solvent. Possible protic solvents are alcohols such as methanol, ethanol, iso-propanol, butanol. Possible aprotic solvents are toluene, tetrahydrofuran, methyl-tetrahydrofuran, methyl tert-butyl ether.

The solid compound of formula I in step e) may be directly isolated by filtering it from the reaction mixture, optionally further contacting the thus isolated solid with water.

Alternatively, the solid compound of formula I in step e) may be isolated by filtering it after contacting the reaction mixture with water.

Alternatively, the solid compound of formula I in step e) may be isolated and/or recovered after dissolution in a suitable organic solvent or mixture of solvents, at a temperature between −5 and 50° C. followed by contacting the thus obtained solution with water. Water may be added to the thus obtained solution or, alternatively, the thus obtained solution may be added to water.

Suitable organic solvents are protic and aprotic dipolar solvents; preferred protic and aprotic dipolar solvents are tetrahydrofuran, methanol, ethanol, isopropanol, butanol, acetone, N,N-dimethylformamide, N-methyl pyrrolidone, acetonitrile, dimethyl sulfoxide, acetic acid.

Preferred solvents used in the isolation of the compound of formula I in step e) wherein $R_2$ is hydroxyethyl are N,N-dimethylformamide and methanol.

In one embodiment, the solid compound of formula I wherein $R_2$ is hydroxyethyl, is isolated by filtration after dissolution of crude intermediate in dimethylformamide followed by contacting the thus obtained solution with water. Water may be added to the thus obtained solution, or alternatively the thus obtained solution may be added to water.

In another embodiment, the solid compound of formula I wherein $R_2$ is hydroxyethyl, is isolated by filtration after contacting the reaction mixture with water, wherein the reaction is preferably performed in presence of methanol. Water may be added to the reaction mixture, or alternatively the reaction mixture may be added to water.

In one embodiment, the solid compound of formula I in step e) wherein $R_2$ is hydrogen is directly isolated by filtering it from the reaction mixture, wherein the reaction is preferably performed in the presence of methanol, and further contacted with water to re-slurry the solid. In one embodiment, the solid compound of formula I in step e) wherein $R_2$ is hydrogen is directly isolated by filtering it from the reaction mixture after contacting the reaction mixture with water. Water may be added to the reaction mixture, or alternatively the reaction mixture may be added to water.

In another object of the present invention the compounds of formula I may be further converted into pharmaceutically acceptable salts thereof.

The aforementioned process may further include the conversion of a compound of formula I into ticagrelor.

In one embodiment, a compound of formula I wherein $R_2$ is hydroxyethyl is converted to ticagrelor by acid hydrolysis.

The acid used for the hydrolysis may be any suitable protic acid. Protic acids include organic and inorganic protic acids. Preferably, the protic acid is an inorganic protic acid, more preferably it is hydrochloric acid, hydrobromic acid, hydroiodic acid or sulfuric acid.

The molar ratio of the compound of formula I to the protic acid is preferably between 0.1 and 0.005, more preferably between 0.015 and 0.010.

In one embodiment, a compound of formula I wherein $R_2$ is hydroxyethyl is suspended in an acidic aqueous medium such as hydrochloric acid 37%, hydrobromic acid 48% and hydroiodic acid 51% at a temperature between 10 and 30° C.

Ticagrelor can be isolated by crystallization of the crude product in a suitable solvent selected from the group comprising water, alcohols, ketones, nitriles, esters, aliphatic ethers, hydrocarbon solvents, chlorinated hydrocarbons and mixture thereof. The preferred solvent is acetonitrile.

In another embodiment, a compound of formula I wherein $R_2$ is hydrogen is converted to ticagrelor via the following steps:

i) reaction with an $C_1$-$C_6$-alkyl haloacetate in the presence of a strong base to give a compound of formula X

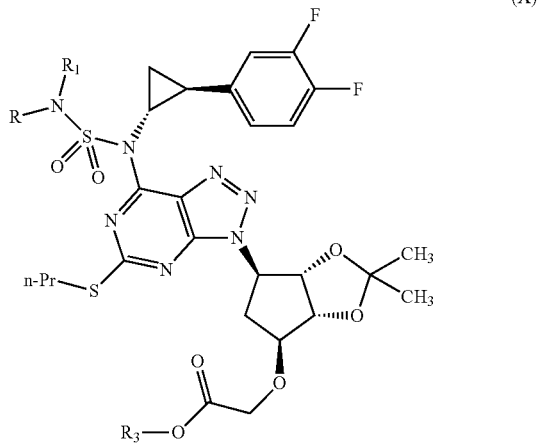

wherein R and $R_1$ are as above defined, and wherein $R_3$ is a $C_1$-$C_6$ alkyl group;

ii) reduction of the compound of formula X to give a compound of formula XI

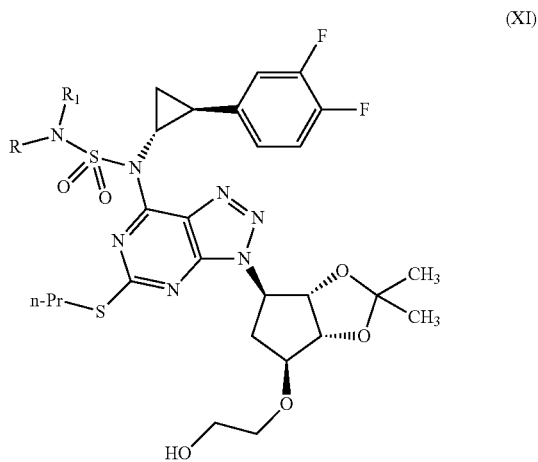

and iii) acid hydrolysis of the compound of formula XI.

The preferred $C_1$-$C_6$-alkyl haloacetate used in step i) is ethyl haloacetate.

Any strong base known to the persons skilled in the art, such as a metal hydride, may be used in step i). More preferably, the strong base is sodium hydride.

The reaction in step i) is carried out in a suitable organic solvent at a temperature between −40° C. and 10° C., more preferably between −25 and −10° C.

The suitable organic solvent is selected from the group comprising acetonitrile, tetrahydrofuran, 2-methyl tetrahydrofuran, 1,4-dioxane, diethyl ether, diisopropyl ether, methyltert-butyl ether, monoglyme, diglyme, n-pentane, n-hexane, n-heptane, cyclohexane, toluene, xylene, N,N-dimethylformamide, N,N-dimethylacetamide, dimethylsulfoxide, N-methylpyrrolidone, and mixtures thereof. The preferred solvent is tetrahydrofuran.

The ratio of the organic solvent to the compound of formula I is preferably between 40 and 10 by weight, more preferably between 30 and 20 by weight.

The molar ratio of the compound of formula I to the $C_1$-$C_6$-alkyl haloacetate is preferably between 1 and 0.1, more preferably between 0.5 and 0.2.

The ester group reduction of step ii) may be performed using any suitable reducing agent for ester groups. The preferred reducing agent for ester groups is sodium borohydride.

The reaction is performed in a suitable organic solvent preferably selected from the group comprising cyclic ethers, aliphatic ethers, chlorinated hydrocarbons, alcohols and mixture thereof.

The ratio of the organic solvent to the compound of formula X is preferably between 50 and 10 by weight, more preferably between 35 and 25 by weight.

Preferably, the reduction is performed in a mixture of tetrahydrofuran and methanol, according to ARKIVOC 2006 (i) 128-133, herein incorporated by reference.

The acid used for the hydrolysis in step iii) may be any suitable protic acid. Protic acids include organic and inorganic protic acids. Preferably, the protic acid is an inorganic protic acid, more preferably it is hydrochloric acid, hydrobromic acid, hydroiodic acid or sulfuric acid.

The molar ratio of the compound of formula XI to the protic acid is preferably between 0.030 and 0.005, more preferably between 0.015 and 0.010.

In one embodiment, a compound of formula XI is suspended in an acidic aqueous medium such as hydrochloric acid 37%, hydrobromic acid 48% and hydroiodic acid 51% at a temperature between 10 and 30° C.

Ticagrelor can be isolated by crystallization of the crude product in a suitable solvent selected from the group comprising water, alcohols, ketones, nitriles, esters, aliphatic ethers, hydrocarbon solvents, chlorinated hydrocarbons and mixture thereof. The preferred solvent is acetonitrile.

In another embodiment, a compound of formula I wherein $R_2$ is a group convertible to hydroxyethyl is converted into ticagrelor via the following steps:

iv) conversion of the group convertible to hydroxyethyl into hydroxyethyl to give a compound of formula XI; and v) acid hydrolysis of the compound of formula XI.

The conversion of the group convertible to hydroxyethyl into hydroxyethyl in step iv) can be performed by using methods known to the person skilled in the art, for instance —$CH_2COOR_3$ by reduction, cyanomethyl and —$CH_2CH(OR^i)(OR^{ii})$ by acid hydrolysis and reduction, silyloxyethyl groups by fluoride cleavage, tert-alkoxyethyl by acid cleavage, benzyloxyethyl by hydrogenation.

In step v) the acid hydrolysis of the compound of formula XI to give ticagrelor is obtained as described above for step iii).

In another object of the present invention ticagrelor may be further converted into pharmaceutically acceptable salts thereof.

An embodiment of the overall process for preparing ticagrelor is summarized in FIG. 1.

The process according to the present invention does not require the isolation and purification of the intermediates by silica gel flash chromatography. The intermediates of the process may instead either be reacted without isolation or isolated as solid by filtration, thus rendering the process conveniently suitable for industrial use.

The compounds formed during the process and the intermediates thereof as above described are novel and represent further aspects of the present invention. Thus, in one embodiment, the present invention provides a compound of formula IV

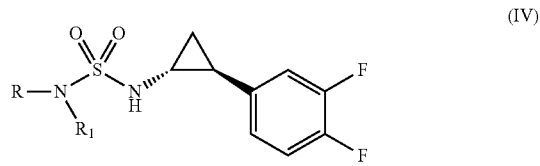

(IV)

wherein R and $R_1$ are independently $C_1$-$C_6$-alkyl or benzyl; or R and $R_1$ are taken together with the nitrogen atom to which they are attached to form a 5 to 6 membered heterocyclic ring, optionally substituted by one or more $C_1$-$C_6$ alkyl group.

In one embodiment, the present invention provides the novel compound of formula IV wherein each R and $R_1$ is a methyl group.

In another embodiment, the present invention provides the novel compound of formula VIII:

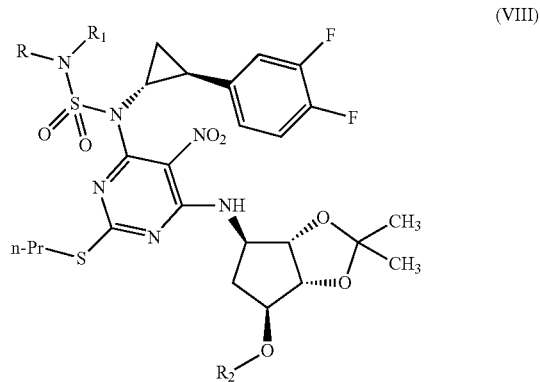

(VIII)

wherein R and $R_1$ are independently $C_1$-$C_6$-alkyl or benzyl; or R and $R_1$ are taken together with the nitrogen atom to which they are attached to form a 5 to 6 membered heterocyclic ring, optionally substituted by one or more $C_1$-$C_6$ alkyl group; and $R_2$ is hydrogen, hydroxyethyl or a group convertible to hydroxyethyl.

In a specific embodiment, the present invention provides the novel compounds of formula VIII wherein each R and $R_1$ is a methyl group and wherein $R_2$ is hydrogen or hydroxyethyl.

A further object of the present invention is represented by the compound of formula IX:

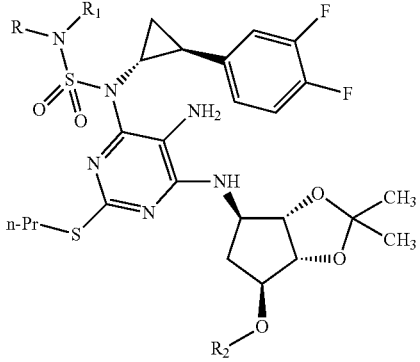

(IX)

wherein R, $R_1$ and $R_2$ are as above defined.

In a specific embodiment, the present invention provides the novel compounds of formula IX wherein each R and $R_1$ is a methyl group and wherein $R_2$ is hydrogen or hydroxyethyl.

Still another object of the invention is represented by the compound of formula I:

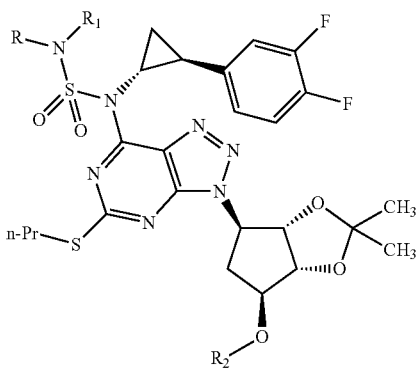

(I)

wherein R, $R_1$ and $R_2$ are as above defined.

In one embodiment, the present invention provides the novel compounds of formula I wherein each R and $R_1$ is a methyl group and wherein $R_2$ is hydrogen or hydroxyethyl.

In another embodiment, the present invention provides a compound of formula X:

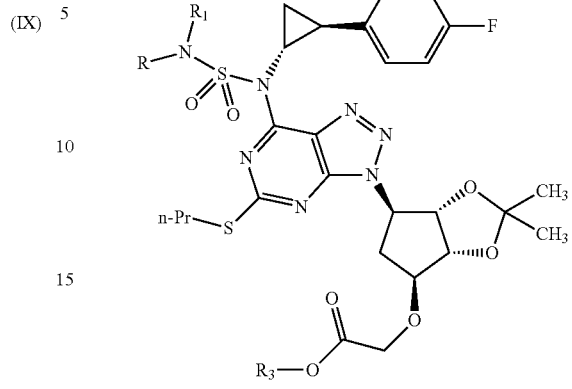

(X)

wherein R and $R_1$ are as above defined and wherein $R_3$ is a $C_1$-$C_6$-alkyl.

In a specific embodiment, the present invention provides the novel compound of formula X wherein each R and $R_1$ is a methyl group and wherein $R_3$ is an ethyl group.

These compounds are intermediates in the process for producing triazolo[4,5-d] pyrimidine cyclopentane compounds and ticagrelor and pharmaceutically acceptable salts thereof according to the present invention.

Another object of the present invention is thus the use of at least one of the compounds (IV), (VIII), (IX), (I) and (X), as intermediates in the synthesis process of triazolo[4,5-d] pyrimidine cyclopentane compounds and of ticagrelor or pharmaceutically acceptable.

A further significant advantage of the present invention resides in the possibility that several synthetic intermediates of the process of the present invention can be isolated as filterable solids from an environmentally benign solvent such as water. This aspect contributes to provide an improved industrially applicable and economically beneficial process for obtaining ticagrelor.

Accordingly, a further aspect the present invention provides a process for the preparation of triazolo[4,5-d] pyrimidine cyclopentane compounds and of ticagrelor or pharmaceutically acceptable salts thereof according to the present invention wherein at least one of the compounds of formula (IV), (VIII), (IX), (I) and (X) is isolated as filterable solid.

EXAMPLES $^1$H NMR spectra were recorded at 303 K, unless otherwise indicated, on a Bruker AMX300 Spectrometer at 300.13 MHz. The chemical shifts were expressed in ppm (parts per million) with tetramethylsilane (TMS) as an internal standard at zero ppm and the coupling constatnts (J) in Hertz. The abbreviations s, d, t, q, m, dd, dt, b refer to singlet, doublet, triplet, multiplet, double doublet, double triplet and broad, respectively.

LC-MS analyzes were carried out using a 6530 Accurate-Mass Q-TOF mass analyzer (Agilent Technologies) coupled with a 1260 HPLC (Agilent Technologies) and a G1315D 1260 DAD VL Photodiode Array Detector (Agilent Technologies).

Example 1

N'-[(1R,2S)-2-(3,4-di fluorophenyl)cyclopropyl]-N,N-dimethylsulfuric diamide A solution was prepared by dissolving NaOH (10.08 g, 0.25 mol) in $H_2O$ (100 mL); toluene (200 mL) and trans-(1R,2S)-2-(3,4-difluorophenyl)-cyclopropylamine (R)-(−)-mandelate salt (67.47 g, 0.21 mol) were added and the mixture was stirred for 15 min. The organic layer was separated and the aqueous phase was extracted with toluene (100 mL). To the combined toluenic phases, 1,4-diazabicyclo[2.2.2]octane (4.71 g, 0.04 mol) was added and toluene (100 mL) was removed by evaporation under reduced pressure. The temperature of the mixture was set to 10° C. N,N-dimethylsulfamoyl chloride (33.17 g, 0.23 mol) was added drop wise keeping the temperature below 20° C. and the reaction mixture was stirred for 1 hour. Water (100 mL) was added and, after stirring the mixture for 15 min, the aqueous layer was separated. Water was added to the organic layer, the pH was set to 2~3 under stirring using concentrated hydrochloric acid. The organic layer was separated and the solvent was removed under reduced pressure to give an oil. Heptane (250 mL) was charged and the slurry was stirred at 20~25° C. for 2 hours. The obtained solid was collected by filtration and dried in vacuo at 40° C. for 4 hours to affording title compound (55.80 g, 96% yield) as a white solid.

1H NMR δ ppm (300 MHz, d6-DMSO): 7.74 (1H, d, J=3.0 Hz, NH); 7.30 (1H, m); 7.18 (1H, m); 6.95 (1H, m); 2.70 (6H, s); 2.56 (1H, m); 2.19 (1H, m); 1.24-1.10 (2H, in).

LC-MS (EST) m/z 277.082 $(MH)^+$

Example 2

N-[(1R,2S)-2-(3,4-difluorophenyl)cyclopropyl]-N-[6-{[(3aS,4R,6S,6aR)-6-(2-hydroxyethoxy)-2,2-dimethyltetrahydro-3aH-cyclopenta[d][1,3]dioxol-4-yl]amino}-5-nitro-2-(propylsulfanyl)pyrimidin-4-yl]-N',N'-dimethylsulfuric diamide In a glass reactor, under a nitrogen atmosphere, 4,6-dichloro-5-nitro-2-(propylthio) pyrimidine (80.00 g, 0.28 mol) and $K_3PO_4$ (89.97, 0.42 mol) were suspended in acetonitrile (1.2 L). N'-[(1R,2S)-2-(3,4-difluorophenyl)cyclopropyl]-N,N-dimethylsulfuric diamide achieved according to the procedure of example 1 (78.31 g, 0.28 mol), was added portion wise and the mixture was stirred at 25° C. for 24 hours. 2-((3aR,4S,6R,6aS)-6-amino-2,2-dimethyl-tetrahydro-3-aH-cyclopenta[d][1,3]dioxol-4-yloxy)ethanol tartaric acid salt (128.81 g, 0.34 mol), $K_3PO_4$ (72.34 g, 0.34 mol) and acetonitrile (0.12 L) were added and the mixture was stirred at 40° C. for further 20 hours. The reaction mixture was diluted with water (1.0 L) and extracted with tert-butyl methyl ether (1.4 L). The organic phase was separated and washed twice with saturated. sodium bicarbonate solution (0.8 L). The organic phase was separated, washed with 1/1 water/brine mixture (0.8 L) and concentrated under reduced pressure. N,N-dimethylformamide (0.25 L) was added and low boiling solvent were evaporated under reduced pressure. The solution was added drop wise to water (2.5 L) under vigorous stirring. After stirring 24 hours at 25° C. the solid was recovered by filtration and washed with water. After dying at 50° C. for 14 hours, title compound (194.00 g, assay 89.4%, 89% yield) was obtained as a yellow solid.

LC-MS (ESI) m/z 689.223 $(MH)^+$

Example 3

N-[(1R,2S)-2-(3,4-difluorophenyl)cyclopropyl]-N-[6-{[(3aS,4R,6S,6aR)-6-(2-hydroxyethoxy)-2,2-dimethyltetrahydro-3aH-cyclopenta[d][1,3]dioxol-4-yl]amino}-5-nitro-2-(propylsulfanyl)pyrimidin-4-yl]-N',N'-dimethylsulfuric diamide In a glass reactor, under a nitrogen atmosphere, 4,6-dichloro-5-nitro-2-(propylthio) pyrimidine (10.00 g, 0.035 mol) and $K_3PO_4$ (11.25, 0.053 mol) were suspended in acetonitrile (150 mL). N'-[(1R,2S)-2-(3,4-difluorophenyl)cyclopropyl]-N,N-dimethylsulfuric diamide achieved according to the procedure of example 1 (9.80 g, 0.035 mol), was added portion wise and the mixture was stirred at 25° C. for 24 hours. 2-((3aR,4S,6R,6aS)-6-amino-2,2-dimethyl-tetrahydro-3aH-cyclopenta[d][1,3]dioxol-4-yloxy)ethanol tartaric acid salt (16.0 g, 0.042 mol), $K_3PO_4$ (9.04 g, 0.042 mol) and acetonitrile (15 mL) were added and the mixture was stirred for further 8 hours. The reaction mixture was diluted with water (200 mL) and extracted with methyl tert-butyl ether (200 mL). The organic phase was separated, washed with saturated sodium bicarbonate solution (100 mL) and concentrated. The crude was purified by silica gel chromatography (eluent hexane/ethyl acetate 6/4) to yield title compound as yellow foam (21.60 g, 89% yield).

1H NMR δ ppm (300 MHz, CDCl3): 8.59 (1H, d, J=6.0 Hz); 7.13-6.94 (3H, m); 4.75 (1H, bt); 4.67 (1H, dd, J=6.0, 1.0 Hz); 4.56 (1H, bd, J=3.6 Hz); 3.98 (1H, d, J=3 Hz); 3.91-3.72 (3H, m); 3.66-3.58 (1H, m); 3.18-2.75 (9H, m); 2.38 (1H, bs); 2.35 (1H, ddd, J=15.0, 6.0, 5.5 Hz); 2.06 (2H, bs), 1.95 (1H, d); 1.78 (2H, m); 1.46 (s, 3H); 1.32 (m, 1H) 1.30 (3H, s); 1.05 (3H, t, J=9.0 Hz).

LC-MS (EST) m/z 689.223 $(MH)^+$

Example 4

N-[5-amino-6-{[(3aS,4R,6S,6aR)-6-(2-hydroxyethoxy)-2,2-dimethyltetrahydro-3aH-cyclopenta[d][1,3]dioxol-4-yl]amino}-2-(propylsulfanyl)pyrimidin-4-yl]-N-[(1R,2S)-2-(3,4-difluorophenyl)cyclopropyl]-N',N'-dimethylsulfuric diamide N-[(1R,2S)-2-(3,4-difluorophenyl)cyclopropyl]-N-[6-{[(3aS,4R,6S,6aR)-6-(2-hydroxyethoxy)-2,2-dimethyltetrahydro-3aH-cyclopenta[d][1,3]dioxol-4-yl]amino}-5-nitro-2-(propylsulfanyl)pyrimidin-4-yl]-N',N'-dimethylsulfuric diamide achieved according to the procedure of example 2 (194.18 g, 0.25 mol) was submitted to hydrogenation using 10% palladium-on-carbon (17.50 g, 50% in water) in methanol (1.2 L) at a pressure of 3 bar. After 8 hours, catalyst was filtered off and the solvents were removed affording the title compound as a brown foam (175.70 g, assay 89%, 94% yield).

LC-MS (ESI) m/z 659.249 $(MH)^+$

Example 5

N-[(1R,2S)-2-(3,4-difluorophenyl)cyclopropyl]-N-{3-[(3aS,4R,6S,6aR)-6-(2-hydroxyethoxy)-2,2-dimethyltetrahydro-3aH-cyclopenta[d][1,3]dioxol-4-yl]-5-(propylsulfanyl)-3H-[1,2,3]triazolo[4,5-d]pyrimidin-7-yl}-N',N'-dimethylsulfuric diamide In a glass reactor, crude N-[5-amino-6-{[(3aS,4R,6S,6aR)-6-(2-hydroxyethoxy)-2,2-dimethyltetrahydro-3aH-cyclopenta[d][1,3]dioxol-4-yl]amino}-2-(propylsulfanyl)pyrimidin-4-yl]-N-[(1R,2S)-2-(3,4-difluorophenyl)cyclopropyl]-N',N'-dimethylsulfuric diamide achieved according to the procedure of example 4 (64.40 g, 0.087 mol) was dissolved in 2/1 methanol/acetic acid mixture (150 mL), NaNO$_2$ (7.35 g, 0.10 mol) was added and the mixture was stirred at room temperature for 4 hours. The reaction mixture was partitioned between water and toluene. The organic phase was washed with saturated sodium bicarbonate solution separated and concentrated. The crude was dissolved in N,N-dimethylformamide (65 mL) and concentrated in vacuo. The obtained solution was added dropwise to water (650 mL) at 0° C. under vigorous stirring. After stirring 1 hour at 0° C. the solid was recovered by filtration and washed with water. After dying at 40° C. for 14 hours, title compound was obtained as a brown solid (52.40 g, 90% yield).

1H NMR: δ ppm (d6-DMSO): 7.28-7.24 (2H, m); 7.08-7.04 (1H, m); 5.26 (1H, dd, J=4.6, 7.0 Hz); 5.19-5.12 (1H, m); 4.70 (1H, dd, J=2.8, 7.1 Hz); 4.54 (1H, m); 4.04 (1H, dt, J=2.9, 7.6 Hz); 3.56 (m, 1H); 3.51-3.38 (4H, m); 3.13 (2H, m); 2.95 (6H, s); 2.76-2.58 (2H, m); 2.44 (1H, ddd, J=3.1, 7.0, 9.7 Hz); 1.81-1.61 (3H, m); 1.51 (3H, s); 1.45 (1H, m); 1.28 (3H, s); 1.01 (3H, t, J=7.3 Hz).

LC-MS (ESI) m/z 670.229 (MH)$^+$

Example 6

N-[(1R,2S)-2-(3,4-difluorophenyl)cyclopropyl]-N-{3-[(3aS,4R,6S,6aR)-6-(2-hydroxyethoxy)-2,2-dimethyltetrahydro-3aH-cyclopenta[d][1,3]dioxol-4-yl]-5-(propylsulfanyl)-3H-[1,2,3]triazolo[4,5-d]pyrimidin-7-yl}-N',N'-dimethyl sulfuric diamide In a glass reactor, to crude N-[5-amino-6-{[(3aS,4R,6S,6aR)-6-(2-hydroxyethoxy)-2,2-dimethyltetrahydro-3aH-cyclopenta[d][1,3]dioxol-4-yl]amino}-2-(propylsulfanyl)pyrimidin-4-yl]-N-[(1R,2S)-2-(3,4-difluorophenyl)cyclopropyl]-N',N'-dimethylsulfuric diamide achieved according to the procedure of example 4 (64.40 g, 0.087 mol) in methanol (185 mL), NaNO$_2$ (7.35 g, 0.10 mol) was added. After cooling the reaction mixture to 18° C., acetic acid (50 mL) was added drop wise. The mixture was stirred at the same temperature for 4 hours. The reaction mixture was added drop wise to water (611 mL) at 0° C. under vigorous stirring. After stirring 16 hours at 0° C. the solid was recovered by filtration and washed with water. After dying at 40° C. for 14 hours, title compound was obtained as a brown solid (62.20 g, 84% yield).

LC-MS (ESI) ink 670.229 (MH)$^+$

Example 7

(1S,2S,3R,5S)-3-[7-{[(1R,2S)-2-(3,4-difluorophenyl)cyclopropyl]amino}-5-(propylsulfanyl)-3H-[1,2,3]triazolo[4,5-d]pyrimidin-3-yl]-5-(2-hydroxyethoxy)cyclopentane-1,2-diol (ticagrelor)

In a glass reactor, a precooled at 0° C., hydrochloric acid solution (124 mL, 37%) was added to crude N-[(1R,2S)-2-(3,4-difluorophenyl)cyclopropyl]-N-{3-[(3aS,4R,6S,6aR)-6-(2-hydroxyethoxy)-2,2-dimethyltetrahydro-3 aH-cyclopenta[d][1,3]dioxol-4-yl]-5-(propylsulfanyl)-3H-[1,2,3]triazolo[4,5-d]pyrimidin-7-yl}-N',N'-dimethylsulfuric diamide achieved according to the procedure of example 5 (7.80 g, 0.010 mol). The mixture was stirred at room temperature for 6.5 hours. Water (300 mL) and methyl tert-butyl ether (200 mL), were added and the mixture was stirred for 10 min. The organic layer was separated and the aqueous phase was extracted twice with methyl tert-butyl ether (200 mL). Combined organic layer were washed with water (200 mL) and with satd. sodium bicarbonate solution (2×100 mL). The organic layer was separated and concentrated to give a brown oil. Acetonitrile (2×50 mL) was added and evaporated under reduced pressure, the crude was suspended in acetonitrile (21 mL) heated at 60° C. until complete dissolution of the solid. Upon cooling the mixture at room temperature, title compound precipitates as an off-white solid. The solid was recovered by filtration and dried in vacuo at 40° C. for 16 hours, affording ticagrelor (3.50 g, 67% yield).

LC-MS (ESI) m/z 523.193 (MH)$^+$

Example 8

N-[(1R,2S)-2-(3,4-difluorophenyl)cyclopropyl]-N-[6-{[(3aS,4R,6S,6aR)-6-hydroxy-2,2-dimethyltetrahydro-3aH-cyclopenta[d][1,3]dioxol-4-yl]amino}-5-nitro-2-(propylsulfanyl)pyrimidin-4-yl]-N',N'-dimethylsulfuric diamide In a glass reactor, under a nitrogen atmosphere, 4,6-dichloro-5-nitro-2-(propylthio) pyrimidine (3.00 g, 0.011 mol) and K$_3$PO$_4$ (3.37 g, 0.016 mmol) were suspended in acetonitrile (42 mL). N'-[(1R,2S)-2-(3,4-difluorophenyl)cyclopropyl]-N,N-dimethylsulfuric diamide achieved according to the procedure of example 1 (2.94 g, 0.011 mol), was added portion wise and the mixture was stirred at 25° C. for 9 hours. (3aR,4S,6R,6aS)-6-amino-2,2-dimethyl-tetrahydro-3aH-cyclopenta[d][1,3]dioxol-4-ol (2.28 g, 0.013 mol), K$_3$PO$_4$ (2.70 g, 0.013 mol) and acetonitrile (3 mL) were added and the mixture was stirred for further 8 hours. The reaction mixture was diluted with water (50 mL) and extracted with methyl tert-butyl ether (50 mL). The organic phase was separated and concentrated under reduced pressure. The crude was dissolved in N,N-dimethylformamide (5 mL), low boiling solvent were evaporated and the obtained solution is added drop wise to water (50 mL) under vigorous stirring. After stirring 24 hours at 25° C. the solid was recovered by filtration and washed with water. After dying at 40° C. for 24 hours, title compound was obtained as a yellow solid (5.78 g, 84% yield).

LC-MS (ESI) m/z 645.197 (MH)$^+$

A sample of the crude was purified by silica gel chromatography (eluent hexane/ethyl acetate from 9/1 to 8/2) for analytical purpose.

1H NMR δ ppm (300 MHz, d6-DMSO): 8.62 (1H, d, J=7.8 Hz); 7.71-7.13 (2H, m); 7.05 (1H, m); 5.74 (1H); 4.57-4.47 (3H); 4.12 (1H, bs), 3.11 (1H, m); 2.88 (8H, bs,); 2.17 (dt, 2H); 1.64 (5H, m); 1.35 (3H, s); 1.21 (3H, s); 0.91 (3H, bs).

LC-MS (ESI) m/z 645.197 (MH)$^+$

Example 9

N-[5-amino-6-{[(3aS,4R,6S,6aR)-6-hydroxy-2,2-dimethyltetrahydro-3aH-cyclopenta[d][1,3]dioxol-4-yl]amino}-2-(propylsulfanyl)pyrimidin-4-yl]-N-[(1R,2S)-2-(3,4-difluorophenyl)cyclopropyl]-N',N'-dimethylsulfuric diamide In a steel autoclave N-[(1R,2S)-2-(3,4-difluorophenyl)cyclopropyl]-N-[6-{[(3aS,4R,6S,6aR)-6-hydroxy-2,2-dimethyltetrahydro-3aH-cyclopenta[d][1,3]dioxol-4-yl]amino}-

5-nitro-2-(propylsulfanyl)pyrimidin-4-yl]-N',N'-dimethylsulfuric diamide achieved according to the procedure of example 8 (3.00 g, 0.005 mol) was dissolved in methanol (75 mL). The mixture was hydrogenated at 3 bar, in the presence of 10% palladium-on-carbon (0.30 g, 50% in water) at room temperature for 16 hours. Catalyst was filtered off and the filtrated was concentrated under reduced pressure. The crude product was purified by silica gel flash chromatography (eluent hexane/ethyl acetate=7/3) affording the title compound (2.60 g, 89% yield) as an off-white foam.

LC-MS (ESI) m/z=615.228 (MH)+

Example 10

N-[(1R,2S)-2-(3,4-difluorophenyl)cyclopropyl]-N-{3-[(3 aS,4R,6S,6aR)-6-hydroxy-2,2-dimethyltetrahydro-3aH-cyclopenta[d][1,3]dioxol-4-yl]-5-(propylsulfanyl)-3H-[1,2,3]triazolo[4,5-d]pyrimidin-7-yl}-N',N'-dimethylsulfuric diamide N-[5-amino-6-{[(3aS,4R,6S,6aR)-6-hydroxy-2,2-dimethyltetrahydro-3aH-cyclopenta[d][1,3]dioxol-4-yl]amino}-2-(propylsulfanyl)pyrimidin-4-yl]-N-[(1R,2S)-2-(3,4-difluorophenyl)cyclopropyl]-N',N'-dimethylsulfuric diamide achieved according to the procedure of example 9 (0.90 g, 1.37 mmol) was dissolved in acetic acid (4.5 mL), NaNO₂ (0.16 g, 1.64 mmol) was added and the mixture was stirred at room temperature for 1 hour. Acetic acid was evaporated under reduced pressure and the residue was partitioned between water (45 mL) and methyl tert-butyl ether (45 mL). The organic phase was washed with saturated sodium bicarbonate solution (15 mL) separated and concentrated. The crude was purified by silica gel flash chromatography (eluent heptane/ethyl acetate=8/2) to afford the title compound (0.80 g, 90% yield) as an off-white foam.

1H NMR δ ppm (300 MHz, d6-DMSO): 7.38-7.12 (2H, m); 7.05 (1H, m); 5.30-5.24 (2H, m); 5.11 (1H, m); 4.56 (1H, dd); 4.17 (1H, m); 3.57 (1H, m); 3.14 (2H, dt); 2.95 (6H, s); 2.58 (2H, m); 2.43 (1H, m); 1.8-1.16 (3H, m); 1.48 (3H, s); 1.45 (1H, m); 1.26 (3H, s); 1.01 (3H, t).

LC-MS (ESI) m/z=626.202 (MH)+.

Example 11

N-[(1R,2S)-2-(3,4-difluorophenyl)cyclopropyl]-N-{3-[(3aS,4R,6S,6aR)-6-hydroxy-2,2-dimethyltetrahydro-3aH-cyclopenta[d][1,3]dioxol-4-yl]-5-(propylsulfanyl)-3H-[1,2,3]triazolo[4,5-d]pyrimidin-7-yl}-N',N'-dimethylsulfuric diamide In a nitrogen atmosphere, NaNO₂ (2.67 g, 0.038 mol) was added to solution of N-[5-amino-6-{[(3 aS,4R,6S,6aR)-6-hydroxy-2,2-dimethyltetrahydro-3 aH-cyclopenta[d][1,3]dioxol-4-yl]amino}-2-(propylsulfanyl)pyrimidin-4-yl]-N-[(1R,2S)-2-(3,4-difluorophenyl)cyclopropyl]-N',N'-dimethyl sulfuric diamide achieved according to the procedure of example 9 in methanol (75.00 g, 0.032 mol). After cooling the mixture to 0° C., acetic acid (18 mL) was added drop wise. The mixture was stirred at room temperature for 16 hours. The product precipitates as a solid in the reaction mixture. The solid was recovered by filtration and washed with methanol (20 mL). The obtained crude was stirred in water (100 mL) at room temperature for 2 hours. The solid was recovered by filtration and dried at 40° C. for 16 hours, affording title compound (12.50 g, 60% yield) as an off white solid.

LC-MS (ESI) m/z=626.202 (MH)+.

Example 12

Ethyl ({(3aR,4S,6R,6aS)-6-[7-{[(1R,2S)-2-(3,4-difluorophenyl)cyclopropyl](dimethylsulfamoyl)amino}-5-(propylsulfanyl)-3H-[1,2,3]triazolo[4,5-d]pyrimidin-3-yl]-2,2-dimethyltetrahydro-3aH-cyclopenta[d][1,3]dioxol-4-yl}oxy)acetate In a glass reactor N-[(1R,2S)-2-(3,4-difluorophenyl)cyclopropyl]-N-{3-[(3aS,4R,6S,6aR)-6-hydroxy-2,2-dimethyltetrahydro-3aH-cyclopenta[d][1,3]dioxol-4-yl]-5-(propylsulfanyl)-3H-[1,2,3]triazolo[4,5-d]pyrimidin-7-yl}-N',N'-dimethylsulfuric diamide achieved according to the procedure of example 10 (1.21 g, 1.94 mmol) was dissolved in dry tetrahydrofuran (33 mL). After cooling the mixture to −20° C., NaH (60% dispersion in mineral oil, 0.12 g, 2.90 mmol) was added and the mixture was stirred for 20 minutes. Ethybromoacetate (0.99 g, 5.81 mmol) was added drop wise and the reaction mixture was stirred at −20° C. for 20 hours. After quenching with acetic acid (2 mL), the reaction mixture was partitioned between water and methyl tert-butyl ether. The organic phase was separated and concentrated to yield a light yellow oil which was purified by silica gel flash chromatography (eluent heptane/ethyl acetate 8/2) to afford the title compound (0.90 g, 64% yield) as an off white foam.

1H NMR δ ppm (300 MHz, d6-DMSO): 7.50-7.19 (2H, m); 7.04 (1H, m); 5.28 (1H, dd); 5.15 (1H, m); 4.76 (1H, dd); 4.19-4.04 (5H, m); 3.57 (1H, m); 3.11 (2H, bt); 2.95 (6H, s); 2.71 (2H, m); 2.43 (1H, m); 1.81-1.61 (3H, m); 1.49 (3H, s); 1.43 (1H, m); 1.28 (3H, s), 1.19 (3H, t); 1.01 (3H, t).

LC-MS (ESI) m/z=712.239 (MH)+

Example 13

N-[(1R,2S)-2-(3,4-difluorophenyl)cyclopropyl]-N-{3-[(3aS,4R,6S,6aR)-6-(2-hydroxyethoxy)-2,2-dimethyltetrahydro-3aH-cyclopenta[d][1,3]dioxol-4-yl]-5-(propylsulfanyl)-3H-[1,2,3]triazolo[4,5-d]pyrimidin-7-yl}-N',N'-dimethylsulfuric diamide (I)

In a glass reactor, in a nitrogen atmosphere, ethyl ({(3aR, 4S,6R,6aS)-6-[7-{[(1R,2S)-2-(3,4-difluorophenyl)cyclopropyl](dimethylsulfamoyl)amino}-5-(propylsulfanyl)-3H-[1,2,3]triazolo[4,5-d]pyrimidin-3-yl]-2,2-dimethyltetrahydro-3aH-cyclopenta[d][1,3]dioxol-4-yl}oxy)acetate achieved according to the procedure of example 12 (0.76 g, 1.05 mmol) was dissolved in tetrahydrofuran (23 mL), NaBH₄ (0.24 g, 6.28 mmol) was added portion wise. The reaction mixture was heated at reflux for 15 min. Then methanol (2.28 mL) was added drop wise and the mixture was stirred at reflux for further 30 min. The reaction mixture was cooled at room temperature, quenched with saturated ammonium chloride solution (1 mL) and stirred at room temperature for 1.5 hours. The mixture was partitioned between water and methyl tert-butyl ether. The organic layer was separated and concentrated under reduced pressure. The crude was purified by silica gel flash chromatography (eluent heptane/ethyl acetate 6/4) affording the title compound (0.48 g, 61% yield) as an off-white foam.

1H NMR δ ppm (300 MHz, d6-DMSO): 7.32-7.19 (2H, m); 7.05 (1H, m); 5.26 (1H, dd); 5.14 (1H, m); 4.70 (1H, dd); 4.54 (1H, m); 4.04 (1H, m); 3.57 (1, m); 3.51-3.38 (4H, m); 3.10 (2H, bt); 2.95 (6H, s); 2.76-2.58 (2H, m); 2.44 (1H, m);

1.80-1.61 (3H, m); 1.51 (3H, s), 1.45 (1H, m), 1.28 (3H, s); 1.01 (3H, t). LC-MS (ESI) m/z=670.228 (MH)+

The invention claimed is:

1. A process for the preparation of a triazolo[4,5-d] pyrimidine cyclopentane compound of formula (I),

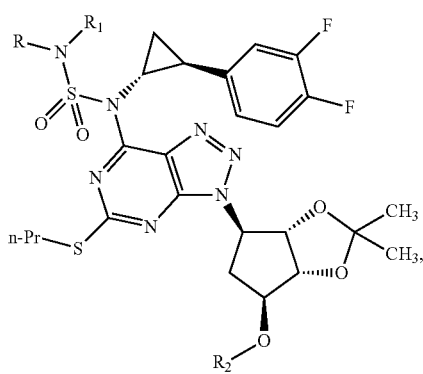

(I)

or a pharmaceutically acceptable salt thereof,
wherein R and $R_1$ are, independently of each other, $C_1$-$C_6$ alkyl or benzyl; or R and $R_1$ are taken together with the nitrogen atom to which they are attached to form a 5 to 6 membered heterocyclic ring, optionally substituted by one or more $C_1$-$C_6$ alkyl group, and $R_2$ is hydrogen, hydroxyethyl or a group convertible to hydroxyethyl, the process comprising the following steps:

a) reacting a compound of formula (II),

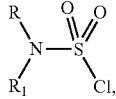

(II)

wherein R and $R_1$ are as above defined, with a compound of formula (III),

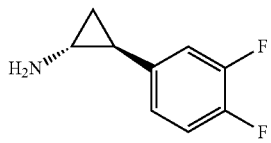

(III)

to obtain a compound of formula (IV),

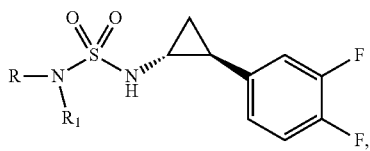

(IV)

wherein R and $R_1$ are as above defined; and
reacting the compound of formula (IV) to obtain the compound of formula (I) or pharmaceutically acceptable salt thereof.

2. The process according to claim 1, wherein step a) is performed in an organic solvent in the presence of a tertiary amine.

3. The process according to claim 2, wherein the organic solvent is toluene and/or the tertiary amine is selected from the group consisting of triethylamine, diisopropylethylamine, 1,8-diazabicyclo[5.4.0]undec-7-ene, 1,4-diazabicyclo[2.2.2]octane and mixtures thereof.

4. The process according to claim 1, further comprising the following step:

b) reacting the compound of formula (IV) with a compound of formula (V),

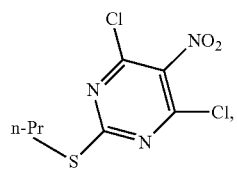

(V)

to obtain a compound of formula (VI),

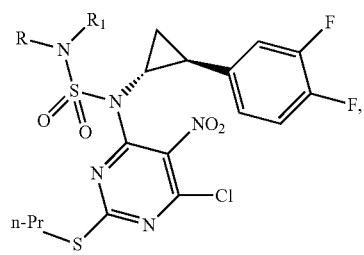

(VI)

wherein R and $R_1$ are as defined in claim 1.

5. The process according to claim 4, further comprising the following step:

c) reacting the compound of formula (VI) with a compound of formula (VII) or a salt thereof,

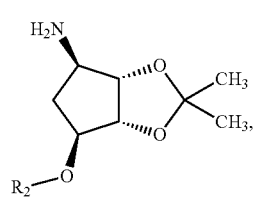

(VII)

wherein $R_2$ is hydrogen, hydroxyethyl or a group convertible to hydroxyethyl, to obtain a compound of formula (VIII),

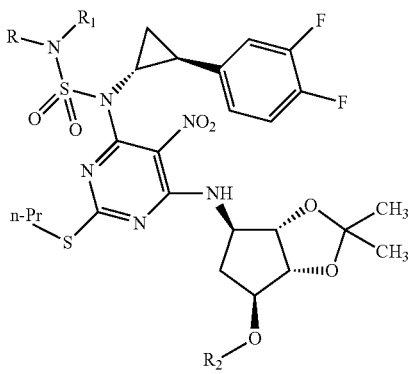

(VIII)

wherein R and R₁ are as defined in claim 4, and R² is as defined above.

6. The process according to claim 5, further comprising the following step:
d) reducing the nitro group of the compound of formula (VIII) to obtain a compound of formula (IX),

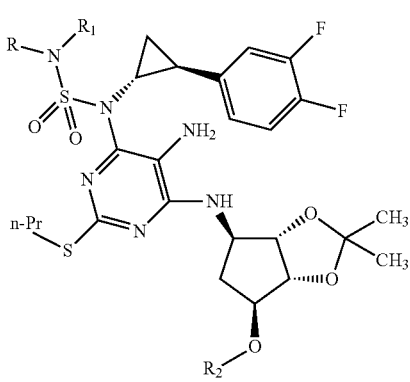

(IX)

wherein R, R₁ and R² is as defined in claim 5.

7. The process according to claim 6, further comprising the following step:
e) nitrosating the compound of the formula (IX).

8. The process according to claim 4, wherein step b) is performed in an organic solvent in the presence of a base.

9. The process according to claim 8, wherein the compound of formula (IV) is isolated as a solid, by filtration after slurring a crude product in an organic solvent, at a temperature between 20 and 40° C.

10. The process according to claim 5, wherein step c) is performed in an organic solvent, in the presence of a base.

11. The process according to claim 10, wherein the compound of formula (VIII) in step c) is isolated as a solid by filtration after dissolution of a crude product in an aprotic dipolar solvent, at a temperature between 10 and 60° C., to obtain a solution, followed by contacting the thus-obtained solution with water.

12. The process according to claim 6, wherein in step d) the reduction is carried out by catalytic hydrogenation in a polar protic solvent in the presence of a palladium catalyst.

13. The process according to claim 7, wherein in step e) the nitrosating reaction is performed with a nitrosating agent in an acidic medium.

14. The process according to claim 13, wherein the compound of formula (I) is isolated as a solid by filtering it from a reaction mixture.

15. The process according to claim 13, wherein the compound of formula (I) wherein R₂ is hydroxyethyl is isolated as a solid after dissolution in an organic solvent to obtain a solution, followed by contacting the obtained solution with water.

16. The process according to claim 1, further comprising converting the compound of formula (I) into ticagrelor.

17. The process according to claim 15, further comprising converting the compound of formula (I) wherein R₂ is hydroxyethyl into ticagrelor by acid hydrolysis.

18. The process according to claim 14, further comprising converting a compound of formula (I) wherein R₂ is hydrogen into ticagrelor via the following steps:
i) reacting the compound of formula (I) wherein R₂ is hydrogen with a $C_1$-$C_6$-alkyl haloacetate in the presence of a strong base to give a compound of formula (X),

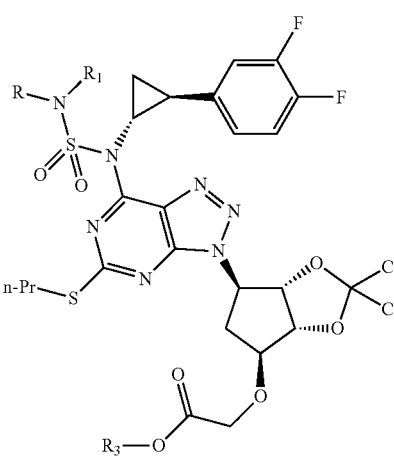

(X)

wherein R and R₁ are, independently of each other, $C_1$-$C_6$-alkyl or benzyl; or R and R₁ are taken together with the nitrogen atom to which they are attached to form a 5 to 6 membered heterocyclic ring, optionally substituted by one or more $C_1$-$C_6$ alkyl group, and wherein R₃ is a $C_1$-$C_6$ alkyl group;

ii) reducing the compound of formula (X) to give a compound of formula (XI),

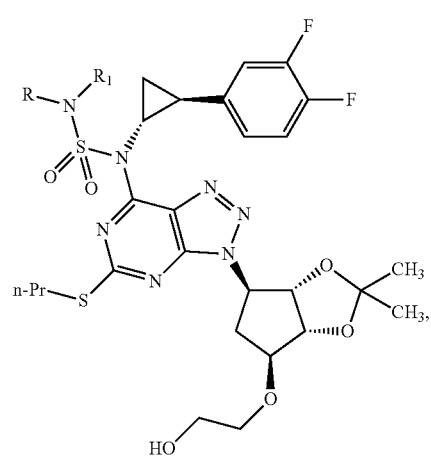

(XI)

and iii) performing an acid hydrolysis of the compound of formula (XI), to obtain the ticagrelor.

19. The process according to claim 14, further comprising converting a compound of formula (I) wherein $R_2$ is a group convertible to hydroxyethyl into ticagrelor via the following steps:

iv) converting the group convertible to hydroxyethyl into hydroxyethyl to obtain a compound of formula (XI); and v) performing acid hydrolysis of the compound of formula (XI), to obtain the ticagrelor.

20. The process according to claim 1, wherein each of R and $R_1$ is a methyl group.

21. A compound of formula (IV),

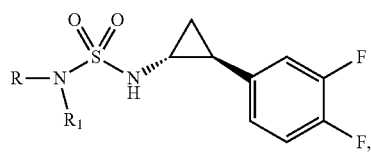

(IV)

wherein R and $R_1$ are independently $C_1$-$C_6$ alkyl or benzyl; or R and $R_1$ are taken together with the nitrogen atom to which they are attached to form a 5 to 6 membered heterocyclic ring, optionally substituted by one or more $C_1$-$C_6$ alkyl group.

22. A compound of the following formula (VIII),

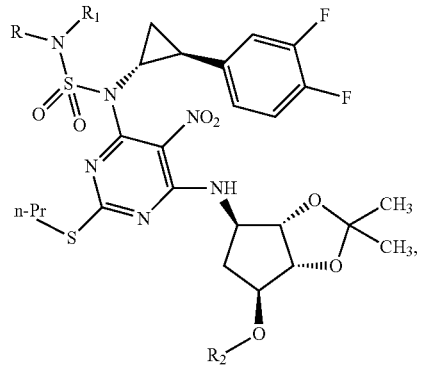

(VIII)

wherein R and $R_1$ are independently $C_1$-$C_6$ alkyl or benzyl; or R and $R_1$ are taken together with the nitrogen atom to which they are attached to form a 5 to 6 membered heterocyclic ring, optionally substituted by one or more $C_1$-$C_6$ alkyl group, and $R_2$ is hydrogen, hydroxyethyl or a group convertible to hydroxyethyl.

23. A compound of the following formula (IX),

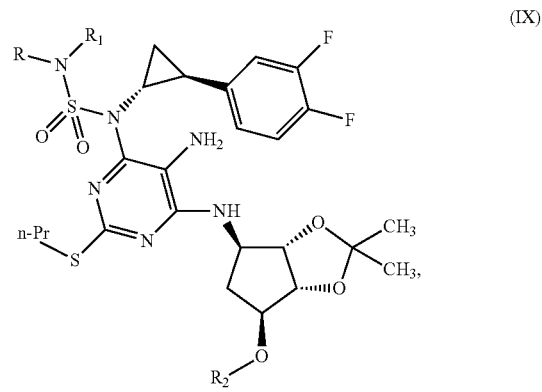

(IX)

wherein R and $R_1$ are independently $C_1$-$C_6$ alkyl or benzyl; or R and $R_1$ are taken together with the nitrogen atom to which they are attached to form a 5 to 6 membered heterocyclic ring, optionally substituted by one or more $C_1$-$C_6$ alkyl group, and $R_2$ is hydrogen, hydroxyethyl or a group convertible to hydroxyethyl.

24. A compound of the following formula (I),

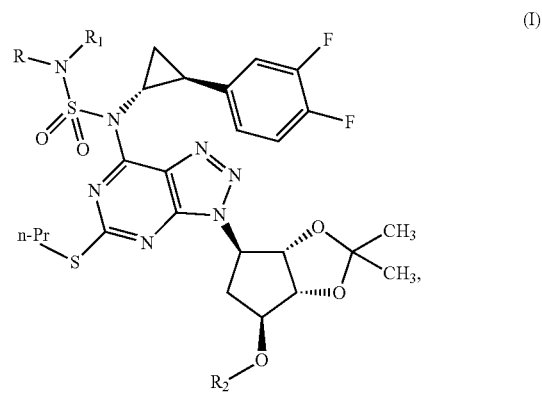

(I)

wherein R and $R_1$ are independently $C_1$-$C_6$-alkyl or benzyl; or R and $R_1$ are taken together with the nitrogen atom to which they are attached to form a 5 to 6 membered heterocyclic ring, optionally substituted by one or more $C_1$-$C_6$ alkyl group, and $R_2$ is hydrogen, hydroxyethyl or a group convertible to hydroxyethyl.

25. A compound of formula (X),

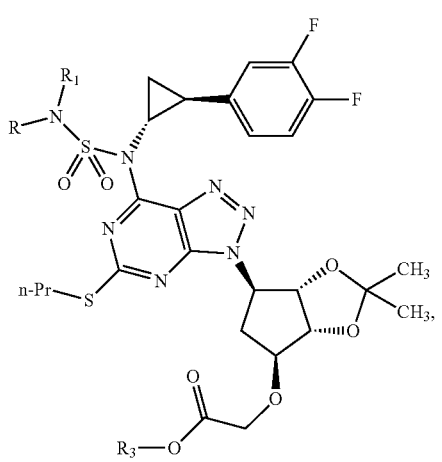

wherein R and $R_1$ are independently $C_1$-$C_6$-alkyl or benzyl; or R and $R_1$ are taken together with the nitrogen atom to which they are attached to form a 5 to 6 membered heterocyclic ring, optionally substituted by one or more $C_1$-$C_6$ alkyl group, and $R_3$ is a $C_1$-$C_6$ alkyl group.

26. The compound according to claim 21, wherein each of R and $R_1$ is a methyl group.

27. The compound according to claim 22, wherein each of R and $R_1$ is a methyl group.

28. The compound according to claim 23, wherein each of R and $R_1$ is a methyl group.

29. The compound according to claim 24, wherein each of R and $R_1$ is a methyl group.

30. The compound according to claim 25, wherein each of R and $R_1$ is a methyl group.

31. A process for the preparation of a triazolo[4,5-d] pyrimidine cyclopentane compound of formula (I),

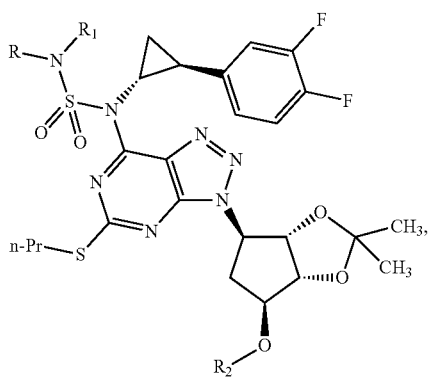

or a pharmaceutically acceptable salt thereof, wherein R and $R_1$ are, independently of each other, $C_1$-$C_6$ alkyl or benzyl; or R and $R_1$ are taken together with the nitrogen atom to which they are attached to form a 5 to 6 membered heterocyclic ring, optionally substituted by one or more $C_1$-$C_6$ alkyl group, and $R_2$ is hydrogen, hydroxyethyl or a group convertible to hydroxyethyl, the process comprising the following steps:

a) reacting a compound of formula (II),

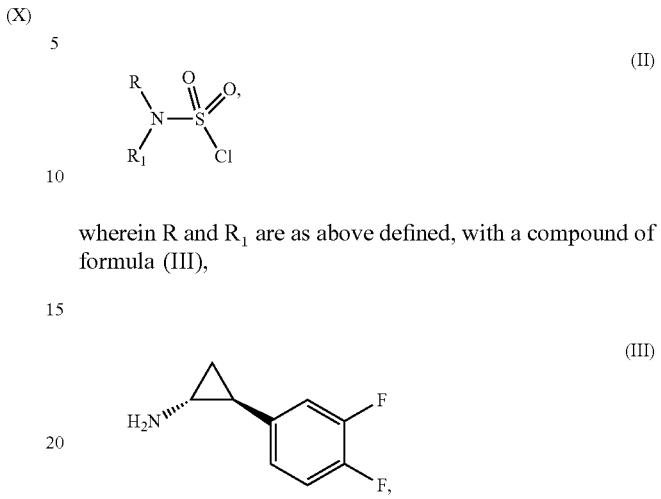

wherein R and $R_1$ are as above defined, with a compound of formula (III),

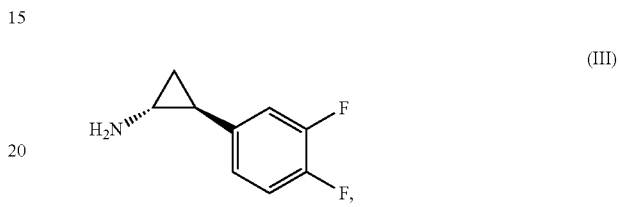

to obtain a compound of formula (IV),

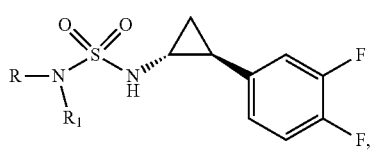

wherein R and $R_1$ are as above defined;

b) reacting the compound of formula (IV) with a compound of formula (V),

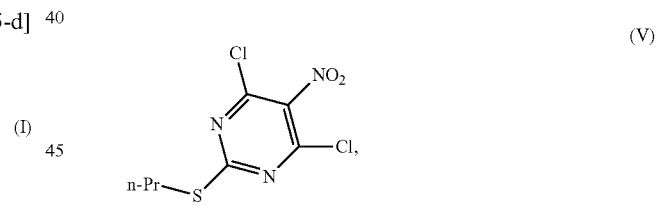

to obtain a compound of formula (VI),

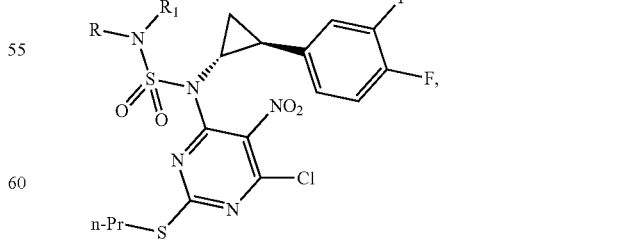

wherein R and $R_1$ are as defined above;

c) reacting the compound of formula (VI) with a compound of formula (VII) or a salt thereof,

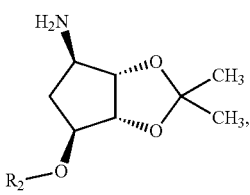

wherein R₂ is as defined above,
to obtain a compound of formula (VIII),

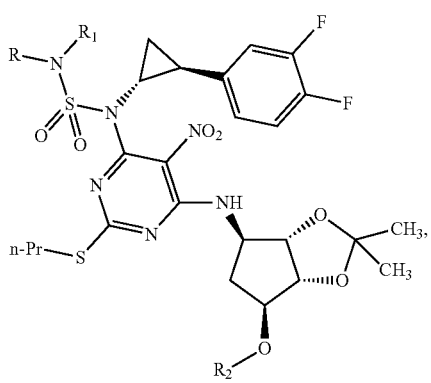

(VIII)

wherein R, R₁ and R₂ are as defined above;
d) reducing the nitro group of the compound of formula (VIII) to obtain a compound of formula (IX),

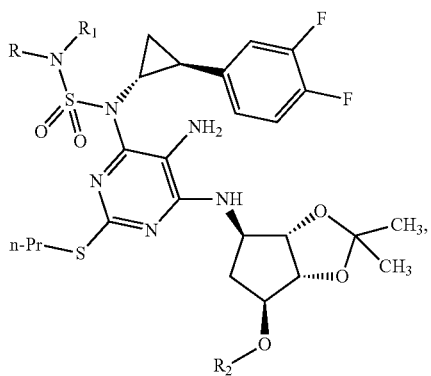

(IX)

wherein R, R₁ and R₂ are as above defined; and e) nitrosating the compound of formula (IX), to obtain the compound of formula (I) or pharmaceutically acceptable salt thereof.

32. A process for the preparation of a compound of formula (IV),

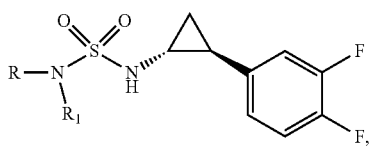

(IV)

or a pharmaceutically acceptable salt thereof, wherein R and R₁ are, independently of each other, C₁-C₆ alkyl or benzyl; or R and R₁ are taken together with the nitrogen atom to which they are attached to form a 5 to 6 membered heterocyclic ring, optionally substituted by one or more C₁-C₆ alkyl group, and R₂ is hydrogen, hydroxyethyl or a group convertible to hydroxyethyl, the process comprising reacting a compound of formula (II),

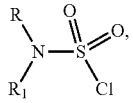

(II)

wherein R and R₁ are as above defined, with a compound of formula (III),

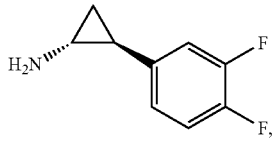

(III)

to obtain the compound of formula (IV) or pharmaceutically acceptable salt thereof.

* * * * *